United States Patent
Birikh et al.

(10) Patent No.: US 10,087,582 B2
(45) Date of Patent: Oct. 2, 2018

(54) METHOD FOR SAVING ENERGY IN PAPER PRODUCTION

(71) Applicant: METGEN OY, Kaarina (FI)

(72) Inventors: Klara Birikh, Kaarina (FI); Alexey Azhayev, Kaarina (FI)

(73) Assignee: METGEN OY, Kaarina (FI)

(*) Notice: Subject to any disclaimer, the term of this patent is extended or adjusted under 35 U.S.C. 154(b) by 315 days.

(21) Appl. No.: 14/778,527

(22) PCT Filed: Mar. 20, 2013

(86) PCT No.: PCT/EP2013/055866
§ 371 (c)(1),
(2) Date: Sep. 18, 2015

(87) PCT Pub. No.: WO2014/146712
PCT Pub. Date: Sep. 25, 2014

(65) Prior Publication Data
US 2016/0069024 A1    Mar. 10, 2016

(51) Int. Cl.
| | | |
|---|---|---|
| *D21B 1/02* | (2006.01) | |
| *D21H 17/00* | (2006.01) | |
| *C12N 9/02* | (2006.01) | |
| *D21C 5/00* | (2006.01) | |
| *D21C 11/00* | (2006.01) | |

(52) U.S. Cl.
CPC ......... *D21H 17/005* (2013.01); *C12N 9/0061* (2013.01); *D21B 1/02* (2013.01); *D21B 1/021* (2013.01); *D21C 5/005* (2013.01); *D21C 11/0007* (2013.01); *C12P 2201/00* (2013.01); *C12Y 110/03002* (2013.01)

(58) Field of Classification Search
CPC ........ D21B 1/02; D21B 1/021; D21H 17/005; D21C 5/005
See application file for complete search history.

(56) References Cited

U.S. PATENT DOCUMENTS

| | | | |
|---|---|---|---|
| 7,566,564 B2 * | 7/2009 | Colpas | C12Q 1/04 435/287.1 |
| 2014/0231034 A1 * | 8/2014 | Blanc | D21B 1/021 162/56 |

FOREIGN PATENT DOCUMENTS

| | | |
|---|---|---|
| WO | 2006121634 | 11/2006 |
| WO | 2010129940 | 11/2010 |

(Continued)

OTHER PUBLICATIONS

Salmen et al., Low sulphonation, energy efficient mechanical pulping—possibilities for process control, 2007, SFTI-Packfoisk report 282.*

(Continued)

*Primary Examiner* — Anthony J Calandra
(74) *Attorney, Agent, or Firm* — Patent Law Works LLP

(57) ABSTRACT

The present invention is in the field of paper production, more in particular it relates to the process of wood pulping. It provides useful biological methods and compounds for reducing the energy requirements of the production of wood pulp. It describes a method for reducing the energy requirement of a thermo-mechanical pulping (TMP) process wherein cellulose fibers are recovered from a biomass comprising lignocellulosic material, wherein the lignocellulosic material is treated with a CotA laccase before recovering the cellulose from the lignocellulosic material.

14 Claims, 8 Drawing Sheets
Specification includes a Sequence Listing.

(56) References Cited

FOREIGN PATENT DOCUMENTS

WO    2013038062    3/2013
WO    2014146712    9/2014

OTHER PUBLICATIONS

PCT International Search Report and Written Opinion dated Nov. 28, 2013, PCT/EP2013/055866.
Martins et al., Molecular and Biochemical Characterization of a Highly Stable Bacterial Laccase That Occurs as a Structural Component of the Bacillus subtilis Endospore Coat, The Journal of Biological Chemistry, May 24, 2002, pp. 18849-18859, vol. 277, No. 21, The American Society for Biochemistry and Molecular Biology, Inc.
Lu et al., UniProt Database, XP-002713754 dated Mar. 6, 2013.
Kasahara et al., Genbank Database, XP-002713763 dated Feb. 13, 1999.
Zeigler D.R., UniProt Database, XP-002716139 dated Mar. 6, 2013.
Lu et al., UniProt Database, XP-002716140 dated Mar. 6, 2013.
Kasahara et al., Sequence Analysis fo the groESL-cotA Region of the Bacillus subtilis Genome, Containing the Restriction/Modification System Genes, Oct. 1, 1997, pp. 335-339, DNA Research 4, Universal Academy Press.
PCT International Preliminary Report on Patentability for PCT/EP2013/055866 dated Sep. 22, 2015.

* cited by examiner

SEQUENCE LISTING

<160> NUMBER OF SEQ ID NOS: 2

<210> SEQ ID NO 1
<211> LENGTH: 513
<212> TYPE: PRT
<213> ORGANISM: Bacillus subtilis

<400> SEQUENCE: 1

```
Met Thr Leu Glu Lys Phe Val Asp Ala Leu Pro Ile Pro Asp Thr Leu
1               5                   10                  15

Lys Pro Val Gln Gln Thr Thr Glu Lys Thr Tyr Tyr Glu Val Thr Met
            20                  25                  30

Glu Glu Cys Ala His Gln Leu His Arg Asp Leu Pro Pro Thr Arg Leu
        35                  40                  45

Trp Gly Tyr Asn Gly Leu Phe Pro Gly Pro Thr Ile Glu Val Lys Arg
    50                  55                  60

Asn Glu Asn Val Tyr Val Lys Trp Met Asn Asn Leu Pro Ser Glu His
65                  70                  75                  80

Phe Leu Pro Ile Asp His Thr Ile His His Ser Asp Ser Gln His Glu
                85                  90                  95

Glu Pro Glu Val Lys Thr Val Val His Leu His Gly Gly Val Thr Pro
            100                 105                 110

Asp Asp Ser Asp Gly Tyr Pro Glu Ala Trp Phe Ser Lys Asp Phe Glu
        115                 120                 125

Gln Thr Gly Pro Tyr Phe Lys Arg Glu Val Tyr His Tyr Pro Asn Gln
    130                 135                 140

Gln Arg Gly Ala Ile Leu Trp Tyr His Asp His Ala Met Ala Leu Thr
145                 150                 155                 160

Arg Leu Asn Val Tyr Ala Gly Leu Val Gly Asp Tyr Ile Ile His Asp
                165                 170                 175
```

```
Pro Lys Glu Lys Arg Leu Lys Leu Pro Ser Gly Glu Tyr Asp Val Pro
            180                 185                 190

Leu Leu Ile Thr Asp Arg Thr Ile Asn Glu Asp Gly Ser Leu Phe Tyr
            195                 200                 205

Pro Ser Gly Pro Glu Asn Pro Ser Pro Ser Leu Pro Lys Pro Ser Ile
210                 215                 220

Val Pro Ala Phe Cys Gly Asp Thr Ile Leu Val Asn Gly Lys Val Trp
225                 230                 235                 240

Pro Tyr Leu Glu Val Glu Pro Arg Lys Tyr Arg Phe Arg Val Ile Asn
                245                 250                 255

Ala Ser Asn Thr Arg Thr Tyr Asn Leu Ser Leu Asp Asn Gly Gly Glu
            260                 265                 270

Phe Ile Gln Ile Gly Ser Asp Gly Gly Leu Leu Pro Arg Ser Val Lys
            275                 280                 285

Leu Asn Ser Phe Ser Leu Ala Pro Ala Glu Arg Tyr Asp Ile Ile Ile
            290                 295                 300

Asp Phe Thr Ala Tyr Glu Gly Glu Ser Ile Ile Leu Ala Asn Ser Glu
305                 310                 315                 320

Gly Cys Gly Gly Asp Ala Asn Pro Glu Thr Asp Ala Asn Ile Met Gln
                325                 330                 335

Phe Arg Val Thr Lys Pro Leu Ala Gln Lys Asp Glu Ser Arg Lys Pro
            340                 345                 350

Lys Tyr Leu Ala Ser Tyr Pro Ser Val Gln Asn Glu Arg Ile Gln Asn
            355                 360                 365

Ile Arg Thr Leu Lys Leu Ala Gly Thr Gln Asp Glu Tyr Gly Arg Pro
370                 375                 380

Val Leu Leu Leu Asn Asn Lys Arg Trp His Asp Pro Val Thr Glu Ala
385                 390                 395                 400

Pro Lys Ala Gly Thr Thr Glu Ile Trp Ser Ile Val Asn Pro Thr Gln
                405                 410                 415

Gly Thr His Pro Ile His Leu His Leu Val Ser Phe Arg Val Leu Asp
            420                 425                 430

Arg Arg Pro Phe Asp Ile Ala Arg Tyr Gln Glu Arg Gly Glu Leu Ser
            435                 440                 445

Tyr Thr Gly Pro Ala Val Pro Pro Pro Ser Glu Lys Gly Trp Lys
450                 455                 460

Asp Thr Ile Gln Ala His Ala Gly Glu Val Leu Arg Ile Ala Val Thr
465                 470                 475                 480

Phe Gly Pro Tyr Ser Gly Arg Tyr Val Trp His Cys His Ile Leu Glu
                485                 490                 495

His Glu Asp Tyr Asp Met Met Arg Pro Met Asp Ile Thr Asp Pro His
            500                 505                 510

Lys

<210> SEQ ID NO 2
<211> LENGTH: 539
<212> TYPE: PRT
<213> ORGANISM: Bacillus subtilis

<400> SEQUENCE: 2

Met Thr Leu Glu Lys Phe Val Asp Ala Leu Pro Ile Pro Asp Thr Leu
1               5                   10                  15

Lys Pro Val Gln Gln Ser Lys Glu Lys Thr Tyr Tyr Glu Val Thr Met
            20                  25                  30
```

```
Glu Glu Cys Thr His Gln Leu His Arg Asp Leu Pro Pro Thr Arg Leu
         35                  40                  45

Trp Gly Tyr Asn Gly Leu Phe Pro Gly Pro Thr Ile Glu Val Lys Arg
 50                  55                  60

Asn Glu Asn Val Tyr Val Lys Trp Met Asn Asn Leu Pro Ser Thr His
 65                  70                  75                  80

Phe Leu Pro Ile Asp His Thr Ile His His Ser Asp Ser Gln His Glu
                 85                  90                  95

Glu Pro Glu Val Lys Thr Val Val His Leu His Gly Gly Val Thr Pro
                100                 105                 110

Asp Asp Ser Asp Gly Tyr Pro Glu Ala Trp Phe Ser Lys Asp Phe Glu
                115                 120                 125

Gln Thr Gly Pro Tyr Phe Lys Arg Glu Val Tyr His Tyr Pro Asn Gln
            130                 135                 140

Gln Arg Gly Ala Ile Leu Trp Tyr His Asp His Ala Met Ala Leu Thr
145                 150                 155                 160

Arg Leu Asn Val Tyr Ala Gly Leu Val Gly Ala Tyr Ile Ile His Asp
                165                 170                 175

Pro Lys Glu Lys Arg Leu Lys Leu Pro Ser Glu Glu Tyr Asp Val Pro
            180                 185                 190

Leu Leu Ile Thr Asp Arg Thr Ile Asn Glu Asp Gly Ser Leu Phe Tyr
            195                 200                 205

Pro Ser Gly Pro Glu Asn Pro Ser Pro Ser Leu Pro Asn Pro Ser Ile
    210                 215                 220

Val Pro Ala Phe Cys Gly Glu Thr Ile Leu Val Asn Gly Lys Val Trp
225                 230                 235                 240

Pro Tyr Leu Glu Val Glu Pro Arg Lys Tyr Arg Phe Arg Val Ile Asn
                245                 250                 255

Ala Ser Asn Thr Arg Thr Tyr Asn Leu Ser Leu Asp Asn Gly Gly Glu
                260                 265                 270

Phe Ile Gln Ile Gly Ser Asp Gly Gly Leu Leu Pro Arg Ser Val Lys
            275                 280                 285

Leu Thr Ser Phe Ser Leu Ala Pro Ala Glu Arg Tyr Asp Ile Ile Ile
    290                 295                 300

Asp Phe Thr Ala Tyr Glu Gly Gln Ser Ile Ile Leu Ala Asn Ser Ala
305                 310                 315                 320

Gly Cys Gly Gly Asp Val Asn Pro Glu Thr Asp Ala Asn Ile Met Gln
                325                 330                 335

Phe Arg Val Thr Lys Pro Leu Ala Gln Lys Asp Glu Ser Arg Lys Pro
            340                 345                 350

Lys Tyr Leu Ala Ser Tyr Pro Ser Val Gln Asn Glu Arg Ile Gln Asn
            355                 360                 365

Ile Arg Thr Leu Lys Leu Ala Gly Thr Gln Asp Glu Tyr Gly Arg Pro
    370                 375                 380

Val Leu Leu Leu Asn Asn Lys Arg Trp His Asp Pro Val Thr Glu Ala
385                 390                 395                 400

Pro Lys Ala Gly Thr Thr Glu Ile Trp Ser Ile Ile Asn Pro Thr Arg
                405                 410                 415

Gly Thr His Pro Ile His Leu His Leu Val Ser Phe Arg Val Ile Asp
                420                 425                 430

Arg Arg Pro Phe Asp Ile Ala His Tyr Gln Glu Ser Gly Ala Leu Ser
            435                 440                 445
```

-continued

```
Tyr Thr Gly Pro Ala Val Pro Pro Pro Ser Glu Lys Gly Trp Lys
    450                 455             460

Asp Thr Ile Gln Ala His Ala Gly Glu Val Leu Arg Ile Ala Ala Thr
465             470                 475             480

Phe Gly Pro Tyr Ser Gly Arg Tyr Val Trp His Cys His Ile Leu Glu
            485                 490             495

His Glu Asp Tyr Asp Met Met Arg Pro Met Asp Ile Thr Asp Pro His
            500             505             510

Lys Ser Asp Pro Asn Ser Ser Ser Val Asp Lys Leu His Arg Thr Arg
        515             520             525

Ala Pro Pro Pro Pro Leu Arg Ser Gly Cys
    530             535
```

METHOD FOR SAVING ENERGY IN PAPER PRODUCTION

FIELD OF THE INVENTION

The present invention is in the field of paper production, more in particular it relates to the process of wood pulping. It provides useful methods and compounds for reducing the energy requirements of the production of wood pulp.

BACKGROUND OF THE INVENTION

Lignin is a major component of wood (seen as brown material), also present in non-wood plants. This heterogeneous polyphenolic compound provides rigidity to the wood structure and protects cellulose fibers from damage. Naturally, lignin creates a major hurdle to recovering cellulose for paper making or other applications. Mechanical pulping of wood is extremely energy intensive process; for example, a typical newsprint pulp may need 2160 kWh of refiner energy per ton of feedstock to refine wood chips into pulp. Reducing this energy requirement is a very acute need of the industry.

As one of the solutions, enzymes capable of oxidizing lignin were proposed to be used for pretreatment of wood chips (material for pulping) in order to decrease the energy required for grinding. This idea was perceived from natural observation that fungi, especially white-rot fungi are able to decay wood material by secreting lignolytic enzymes such as peroxidases and laccases.

This idea was first implemented as so-called bio-pulping, when fungal species were actually cultivated on wood chips before pulping. This resulted in substantial energy saving, but cultivation time comprised several weeks, which was not acceptable in industrial context.

Subsequently, it was proposed to use isolated enzyme preparations for wood pretreatment, rather than live species, which should in principle produce similar effect. This resulted in a limited number of publications wherein isolated fungal laccases were employed for wood chips pretreatment.

There remains a need in the art for enzymes with an improved performance, in terms of cost-effective lignin oxidation, energy saving in the process, speed of action, safety, stability and potential for development.

SUMMARY OF THE INVENTION

Fungal laccases are known to have a high redox potential. Most research efforts described so far were directed towards finding enzymes with even higher redox potential. Surprisingly, we have now found that enzymes with a low to medium redox potential perform better than the conventional fungal laccases. We found that a bacterial laccase (CotA) obtainable from *Bacillus subtilis* has a vastly improved effect on the structural integrity of wood chips, in comparison to fungal laccases or even other bacterial laccases. Consequently, this enzyme is better suited than any other laccase for the pretreatment of wood chips in the paper and pulp industry.

We found that pretreatment of wood chips with CotA laccase reduced the energy requirements of the process of wood pulping.

The invention relates therefore to a method for reducing the energy requirement of a process for recovering cellulose from a biomass comprising a lignocellulosic material, wherein the biomass comprising a lignocellulosic material is treated with a CotA laccase before recovering the cellulose from the biomass.

A suitable process for recovering cellulose from a biomass comprising a lignocellulose material, is a so called thermo-mechanical pulping process (TMP). In such a process, the biomass is heated to a temperature above 100 degrees Celsius and simultaneously subjected to mechanical defibration.

In other terms, the invention relates to a method for recovering cellulose or cellulose fibers from a biomass comprising lignocellulosic material wherein the method comprises a step wherein the biomass is heated to a temperature above 100 degrees Celsius and subjected to mechanical defibration and wherein the biomass comprising lignocellulosic material is contacted with a CotA laccase before it is defibrated.

DETAILED DESCRIPTION OF THE INVENTION

Papermaking is the process of making paper. In papermaking, a dilute suspension of cellulose fibers in water is drained through a screen, so that a mat of randomly interwoven fibers is laid down. Water is removed from this mat of fibers by pressing and drying to make paper. Since the invention of the Fourdrinier machine in the 19th century, most paper has been made from wood pulp because of cost.

Other fiber sources such as cotton and textiles are also used for high-quality papers. One common measure of a paper's quality is its non-woodpulp content, e.g., 25% cotton, 50% rag, etc. Previously, paper was made of rags and kemp as well as other materials. Wood and other plant materials used to make pulp contain three main components (apart from water): cellulose fibers (desired for papermaking), lignin (a three-dimensional polymer that binds the cellulose fibers together) and hemicelluloses, (shorter branched carbohydrate polymers).

Pulping is a process of preparing pulp. Pulp is a material comprised of wood fibers or cellulose fibers.

The aim of pulping is to break down the bulk structure of the fiber source, be it wood chips, stems or other plant parts, into the constituent fibers.

Pulp may be produced in a process called mechanical pulping. For the production of mechanical wood pulp, wood may be ground, such as for instance against a water lubricated rotating stone. The heat generated by grinding softens the lignin binding the fibers and the mechanical forces separate the fibers to form groundwood. This is also referred herein as defibration.

"Defibration" as used herein refers to a process of separating wood fibers from each other.

During the second half of the 20th century, newer mechanical techniques using 'refiners' were developed. In a refiner, woodchips are subjected to intensive shearing forces, for example, between a rotating steel disc and a fixed plate. This is also comprised in the term "defibration".

Mechanical pulp consists of a mix of whole fibers and fiber fragments of different sizes. Mechanical pulp gives the paper a yellowish/grey tone with high opacity and a very smooth surface. Mechanical pulping provides a good yield from the pulpwood because it uses the whole of the log except for the bark, but the energy requirement for refining is high and can only be partly compensated by using the bark as fuel. The various mechanical pulping methods, such as groundwood (GW) and refiner mechanical (RMP) pulping, physically tear the cellulose fibers one from another. Much of the lignin remains adhered to the fibers. Strength of the fibers may be impaired because the fibers may be cut.

In subsequent modifications to this process, the woodchips are pre-softened by heat (thermo-mechanical pulping (TMP)) to make the fibrillation or defibration more effective. The resulting pulp is light-coloured and has longer fibers.

With reference to FIG. 7, Thermo-mechanical pulping (TMP) is a process in which wood chips are heated and run through a mechanical refiner for defibration (fiber separation), resulting in thermo-mechanical pulp.

In a typical TMP process, wood chips are fed to a presteamer and are steamed with process steam (typically 1 to 2 bar or above 100 degrees Celsius, such as 130 to 140 degrees C.) from the refiners. After a retention time of several minutes, the pressurized chips may be fed to the refiner with the feeding screw (plug feeder). The refiner separates the fibers by mechanical force via refiner mechanical means (e.g. between rotating disc plates). The refiner may be fed with fresh steam during startup, to increase the pressure up to 4 or 5 bar and about 150 degrees C.

Thermomechanical pulping therefore refers to a process of producing pulp, which includes heating of biomass to a temperature above 100 degrees Celsius and mechanical defibration.

The term "refine" or "refining" as used herein refers to mechanical defibration at a temperature above 100 degrees Celsius.

The pulp is often refined in two stages. The process steam is typically taken to a heat recovery unit to produce clean steam. The refiner discharges the pulp and steam to a cyclone. The cyclone separates the steam from the pulp.

As used herein, thermo-mechanical pulp is pulp produced by processing wood chips using heat and a mechanical refining movement.

Wood chips are usually produced as follows: the logs are first stripped of their bark and converted into small chips, which have a moisture content of around 25-30%. A mechanical force is applied to the wood chips in a crushing or grinding action which generates heat and water vapour and softens the lignin thus separating the individual fibers.

The pulp is then screened and cleaned, any material that was not sufficiently refined (did not pass in screening procedure) is separated as "reject" and reprocessed. The TMP process gives a high yield of fiber from the timber (around 95%) and as the lignin has not been removed, the fibers are hard and rigid.

Delignification may also be achieved in a chemical process. A typical example is the so-called "Kraft" delignification process, which uses sodium hydroxide and sodium sulfide to chemically remove lignin. After delignification, the color of the pulp is dark brown. If white paper is desired, the pulp is bleached. Delignified, bleached pulp is fed into paper machines after undergoing other chemical processes that produce the desired quality and characteristics for the paper. A chemical pulp or paper is called wood-free, although in practice a small percentage of mechanical fiber is usually accepted.

Chemical pulping applies so called cooking chemicals to degrade the lignin and hemicellulose into small, water-soluble molecules which can be washed away from the cellulose fibers without depolymerizing the cellulose fibers. This is advantageous because the de-polymerization of cellulose weakens the fibers. Using chemical pulp to produce paper is more expensive than using mechanical pulp or recovered paper, but it has better strength and brightness properties.

A further development of chemical pulping and thermo-mechanical pulping is chemical thermo-mechanical pulping (CTMP). Herein, the wood chips are impregnated with a chemical such as sodium sulphite before the refining step. The end result is a light-coloured pulp with good strength characteristics. The chemical and thermal treatments reduce the amount of energy subsequently required by the mechanical refining, and also reduce the loss of strength suffered by the fibers. In CTMP, wood chips can be pretreated with sodium carbonate, sodium hydroxide, sodium sulfite and other chemicals prior to refining with equipment similar to a mechanical mill. The conditions of the chemical treatment are less vigorous (lower temperature, shorter time, less extreme pH) than in a chemical pulping process since the goal is to make the fibers easier to refine, not to remove lignin as in a fully chemical process.

Wood chips for TMP or CTMP are usually obtained from bark free and fresh tree wood. After manufacturing, the chips are screened to have specified size. For superior quality pulp, and optimal energy consumption, chips usually have thickness of 4-6 mm and length (dimension along the fibers) of 10-50 mm, such as 15-40 mm or 16-22 mm. Before refining, the chips are washed and steamed, these chips have a typical moisture content of above 20% such as around 25-30%.

In comparison, mechanical pulping requires a lot of energy, in the range of 1000-3500 kiloWatt per ton of pulp whereas the chemical pulping process is self-sufficient. Chemical pulping yield better (longer) fibers whereas the fibers obtained in mechanical pulping are of different sizes. This results in low paper strength. Production costs of mechanical pulp are much less however in comparison to chemical pulping. Mechanical pulping has a yield of 95% as opposed to 45% of the chemical process. The yield in chemical processes is much lower, as the lignin is completely dissolved and separated from the fibers. However, the lignin from the sulphate and some sulphite processes can be burnt as a fuel oil substitute. In modern mills, recovery boiler operations and the controlled burning of bark and other residues makes the chemical pulp mill a net energy producer which can often supply power to the grid, or steam to local domestic heating plants.

After grinding, the pulp is sorted by screening to suitable grades. It can then be bleached with peroxide for use in higher value-added products.

Freeness is a measure of drainability of a pulp suspension. It characterizes how fine the pulp has been refined. It can be determined by Canadian Standard Freeness—(CSF) Method (Thode, E. F., and Ingmanson, W. L., Tappi 42(1): 74 (1959) especially p. 82.; Technical Section, Canadian Pulp & Paper Association, Official Standard Testing Method C.1, "The Determination of Freeness") and measured in milliliters. Higher CSF numbers mean faster draining, less refined pulp. Energy requirement for refining depends on the targeted freeness. Reaching lower freeness requires more energy. "Energy saving" in refining refers to a situation when the same freeness is achieved with less energy.

As used herein, the term "pulp mill" is a manufacturing facility that converts wood chips or other plant fiber sources into a thick fiber board which can be shipped to a paper mill for further processing. Pulp can be manufactured using mechanical, thermo-mechanical, chemo thermo-mechanical or fully chemical methods. The finished product may be either bleached or non-bleached, depending on the customer requirements.

As used herein, the term "pulp" is intended to mean a lignocellulosic fibrous material prepared by chemically and/ or mechanically separating cellulose fibers from wood, fiber crops or waste paper. Wood pulp is the most common raw material in papermaking.

The term lignocellulosic material refers to a material that comprises (1) cellulose, hemicellulose, or a combination and (2) lignin.

The timber resources used to make wood pulp are referred to as pulpwood. Wood pulp comes from softwood trees such as spruce, pine, fir, larch and hemlock, and hardwoods such as eucalyptus, aspen and birch wood chipping is the act and industry of chipping wood for pulp, but also for other processed wood products and mulch. Only the heartwood and sapwood are useful for making pulp. Bark contains relatively few useful fibers and is removed and used as fuel to provide steam for use in the pulp mill.

Most pulping processes require that the wood be chipped and screened to provide uniform sized chips. Manufactured grindstones with embedded silicon carbide or aluminum oxide can be used to grind small wood logs called "bolts" to make stone ground wood pulp (SGW). If the wood is steamed prior to grinding it is known as pressure ground wood pulp (PGW). Most modern mills use chips rather than logs and ridged metal discs called refiner plates instead of grindstones. If the chips are just ground up with the plates, the pulp is called refiner mechanical pulp (RMP) and if the chips are steamed while being refined the pulp is called thermo-mechanical pulp (TMP). Steam treatment significantly reduces the total energy needed to make the pulp and decreases the damage (cutting) to fibers.

An advantageous effect of applying a mechanical force to the wood chips in a crushing or grinding action (herein also referred to as refining, FIG. 7) is that it generates heat which softens the lignin thus adding in the separation of individual cellulose fibers.

Pretreatment (an optional step in TMP and obligatory in CTMP) is a process when chips are exposed to a certain chemical or enzymatic solution, or a mechanical treatment before refining. The purpose of pretreatment is to reduce refining energy consumption or to improve pulp properties. Physical pretreatment is often called size reduction and is aiming to reduce chips physical size. With reference to FIG. 7 this is also called low energy mechanical treatment. Chemical pretreatment is to remove chemical barriers so the cellulose fibers are more easily recoverable.

The term "low energy mechanical treatment" is used herein to indicate a process wherein the biomass containing the lignocellulosic material is subjected to mechanical forces such that the temperature of the biomass does not exceed 95 degrees Celsius.

Pretreatment is also often done by impregnation. Impregnation is a process when chips are first pressurized and upon slow release of pressure, the pretreatment solution is added to the chips. The pressure can be build up by mechanical force (e.g. impregnation screw) or by a steam-cooker principle. Thus impregnation can sometimes combine chemical and mechanical pretreatment. In industrial conditions impregnation is usually done on steamed chips, which facilitates impregnation. Impregnation improves the penetration of the pretreatment solution inside the wood. Pretreatment may be continued in a reaction vessel following the impregnation stage in the process.

In an alternative procedure, pretreatment includes low energy mechanical treatment (the energy is low as compared to the refining energy) of wood chips to increase the surface of contact with the pretreatment solution. In a low energy mechanical pretreatment, there is no significant production of heat, in other words, the temperature of the wood chips in this step may not exceed 95 degrees C. or less, such as 90, 85, 80, 75, 70, 65, 60, 55, 50, 45, or 40 degrees Celsius.

"Destructured wood chips" are wood chips which were partially destroyed as a result of impregnation or low energy mechanical pretreatment. The term "low energy mechanical pretreatment" in this respect is to be interpreted as a process wherein the wood chips are partially destructured but not fiberized.

We now found that a bacterial laccase (CotA) obtainable from *Bacillus subtilis* has a vastly improved effect on the structural integrity of wood chips, in comparison to fungal laccases or even other bacterial laccases. Consequently, this enzyme is better suited than any other laccase for the pretreatment of wood chips in the paper and pulp industry, in particular in thermo-mechanical pulping.

We found that pretreatment of wood chips with CotA laccase reduced the energy requirements of the process of wood pulping.

The invention relates therefore to a method for reducing the energy requirement of a process for recovering cellulose from a biomass comprising a lignocellulosic material, wherein the biomass comprising a lignocellulosic material is treated with a CotA laccase before recovering the cellulose from the biomass.

A suitable process for recovering cellulose from a biomass comprising a lignocellulose material is a so called thermo-mechanical pulping process. In such a process, the biomass is heated to a temperature above 100 degrees Celsius and simultaneously subjected to mechanical defibration.

In other terms, the invention relates to a method for recovering cellulose fibers from a biomass comprising lignocellulosic material wherein the method comprises a step wherein the biomass is heated to a temperature above 100 degrees Celsius and subjected to mechanical defibration and wherein the biomass comprising lignocellulosic material is contacted with a CotA laccase before it is heated to a temperature above 100 degrees Celsius.

Laccases (EC 1.10.3.2) are enzymes having a wide taxonomic distribution and belonging to the group of multicopper oxidases. Laccases are eco-friendly catalysts, which use molecular oxygen from air to oxidize various phenolic and non-phenolic lignin-related compounds as well as highly recalcitrant environmental pollutants, and produce water as the only side-product. These natural "green" catalysts are used for diverse industrial applications including the detoxification of industrial effluents, mostly from the paper and pulp, textile and petrochemical industries, use as bioremediation agent to clean up herbicides, pesticides and certain explosives in soil. Laccases are also used as cleaning agents for certain water purification systems. In addition, their capacity to remove xenobiotic substances and produce polymeric products makes them a useful tool for bioremediation purposes.

Laccases were originally discovered in fungi, they are particularly well studied in White-rot fungi and Brown-rot fungi. Later on, laccases were also found in plants and bacteria. Laccases have broad substrate specificity; though different laccases can have somewhat different substrate preferences. Main characteristic of laccase enzyme is its redox potential, and according to this parameter all laccases can be divided in three groups (see, for example, Morozova, O. V., Shumakovich, G. P., Gorbacheva, M. a., Shleev, S. V., & Yaropolov, a. I. (2007). "Blue" laccases. Biochemistry (Moscow), 72(10), 1136-1150. doi:10.1134/S0006297907100112): high redox potential laccases (0.7-0.8 V), medium redox potential laccases (0.4-0.7 V) and low redox potential laccases (<0.4V). It is believed that low redox potential limits the scope of substrates which the enzyme can possibly oxidize, and vice versa. All high redox potential laccases and the upper part of the medium redox potential laccases are fungal laccases. Industrial application of laccases is mostly if not entirely relying on fungal laccases.

CotA is a bacterial laccase and is a component of the outer coat layers of *bacillus* endospore. It is a 65-kDa protein encoded by the cotA gene (Martins, O., Soares, M., Pereira, M. M., Teixeira, M., Costa, T., Jones, G. H., & Henriques, A. O. (2002). Molecular and Biochemical Characterization of a Highly Stable Bacterial Laccase That Occurs as a Structural Component of the *Bacillus subtilis* Endospore Coat. Biochemistry, 277(21), 18849-18859. doi:10.1074/jbc.M200827200). CotA belongs to a diverse group of multi-copper "blue" oxidases that includes the laccases. This protein demonstrates high thermostability, and resistance to various hazardous elements in accordance with the survival abilities of the endospore. The redox-potential of this protein has been reported to be around 0.5 mV, which places it in the range of medium-redox-potential laccases.

In the work described herein, we tested the action of different laccases on wood structure to elucidate their potential for wood pretreatment. We applied the same amount of activity units of a high-redox-potential fungal laccase from *Trametes versicolor* (0.78 V), *Escherichia coli* laccase CuEO (0.36 V) and *Bacillus subtilis* CotA laccase (0.5 V).

Microscopic analysis of slices of wood chips pretreated with these laccase revealed that CotA protein has a distinct and profound effect on wood structure different from that inflicted by fungal laccases or other bacterial laccases.

We observed that the wood chips treated with CotA laccase showed more and larger openings between the fiber walls than chips treated with any of the other enzymes. Representative examples are shown in FIGS. 1 to 6. FIG. 1 shows a section of a wood chip at the edge of the chip with cracks in the primary fiber walls (white arrows indicate some of the cracks). These cracks loosen the fibers from each other without damaging them and thus decrease the energy required for pulping, which is essentially separation of fibers from each other (defibration). The cracks will also ensure that the lignin becomes more accessible for other pretreatment chemicals or enzymes thereby improving their efficiency. In FIG. 2, a section at the center of the wood chip treated with a CotA laccase is shown, again showing substantial desirable cracks in the structure (white arrows indicate some of the cracks). In contrast, fungal enzymes and other bacterial enzymes did not show this effect (FIGS. 3-6), underlining the special feature that CotA is exceptionally suitable for wood pretreatment in the preparation of wood pulp for the production of paper.

In terms of primary structure, laccases are highly divers. In many cases laccases may hardly have any significant sequence homology to some other members of multi-copper oxidases. For example, alignment of a CotA laccase from *Bacillus subtilis*, Gen Bank: BAA22774.1 with fungal *Trametes versicolos* laccase (GenBank: CAA77015) using "Blast 2 sequences" online resource (http://blast.ncbi.nlm.nih.gov/Blast.cgi?PAGE=Proteins&PROGRAM=blastp&BLAST_PROGRAMS=blastp&PAGE_TYPE=BlastSearch&BLAST_SPEC=blast2seq) shows that only 54% of the sequence length could be aligned with an identity in the aligned section of 22%. Alignment of CotA laccase from *Bacillus subtilis*, GenBank: BAA22774.1 to another bacterial laccase—CuEO from *E. coli* (ZP_03034325.1) showed only 29% identity.

In contrast, CotA laccases themselves represent a rather compact and well defined group of sequences. We performed Blast search of sequences from the Protein databank (http://blast.ncbi.nlm.nih.gov/Blast.cgi?PROGRAM=blastp&BLAST_PROGRAMS=blastp&PAGE_TYPE=BlastSearch&SHOW_DEFAULTS=on&LINK_LOC=blasthome) having homology to preferred sequences termed COT1 protein (SEQ ID NO: 1) and COT2 protein (SEQ ID NO: 2) as described herein.

This search revealed a highly compact group of sequences showing between 98% and 91% identity to the COT2 sequence. Another group of sequences, which also consisted exclusively of *Bacillus* species spore coat laccases, had an identity between 78% and 82% to the COT1 sequence.

In the group of sequences with an identity of 60% or higher, all sequences were Coat Spore proteins from *Bacillus* species, products of corresponding COTA genes. It may therefore be concluded that CotA does not have any significant sequence identity to other laccases.

For the purpose of this invention, the term "CotA" is defined herein as an isolated protein with laccase activity with a primary amino acid structure that is at least 60% identical to the sequence according to SEQ ID NO: 2. Preferably, CotA has a primary structure that is at least 65% identical to the sequence according to SEQ ID NO: 2, such as at least 70%, 75%, 80%, 85%, 90%, 91%, 92%, 93%, 94%, 95%, 96%, 97%, 98%, 99% or even 100%.

As described in the examples section, we were able to show that wood chips treated with a *Bacillus subtilis* spore coat protein termed CotA were a superior substrate for the preparation of pulp for the paper making industry. The treatment with the CotA polypeptide resulted in a desirable decrease of the strength of the cell wall material of the lignocellulose substrate, such that the energy requirement of the process decreased significantly. This was particularly the case in a thermo-mechanical pulping process.

Hence, the invention relates to a method for reducing the energy requirement of a thermo-mechanical pulping (TMP) process wherein cellulose fibers are recovered from a biomass comprising lignocellulosic material, wherein the lignocellulosic material is treated with a CotA laccase before recovering the cellulose from the lignocellulosic material.

In other terms, the invention relates to a method for recovering cellulose fibers from a biomass comprising lignocellulosic material wherein the method comprises a step wherein the biomass is heated to a temperature above 100 degrees Celsius and subjected to mechanical defibration and wherein the biomass comprising lignocellulosic material is contacted with a CotA laccase before it is heated to a temperature above 100 degrees Celsius.

A particularly preferred substrate in the method according to the invention is wood or wood chips. Hence, in a preferred embodiment, the invention relates to a method as described above wherein the lignocellulosic material comprises or consists of wood, a wood chip or a destructured wood chip.

The method as described above not only decreased the physical strength of the cell walls of the lignocellulosic material, it also makes the lignocellulosic fibers better accessible for other reagents. This was found to be advantageous in a particular embodiment of the TMP process, namely a chemo thermo-mechanical pulping (CTMP) process. Hence, the invention also relates to a method as described above, wherein the TMP is a chemo thermo-mechanical pulping (CTMP) process.

With reference to FIG. 7, a chemo thermo-mechanical pulping process differs from a TMP process in that at least one additional step is added and wherein the biomass containing the lignocellulosic material is impregnated with a chemical composition in order to at least partially degrade lignin.

More in particular, in a preferred embodiment, the invention relates to a method as described above comprising an additional step of treating the biomass comprising the lignocellulosic materials with a chemical before the biomass is subjected to defibration. In a particularly preferred embodiment the chemical is able to degrade lignin.

With reference to FIG. 7, the treatment with the CotA laccase may be employed at different stages in the process. First of all, the lignocellulosic material may be contacted with the enzyme after it has been provided in the appropriate dimensions, optionally after cleaning and steaming. This is indicated with the arrow marked (3) in FIG. 7.

For a process wherein the lignocellulosic material is wood, this means that the wood is treated after it is debarked and chopped in pieces and selected for size. These pieces are usually referred to as wood chips. Such wood chips typically have a largest dimension of typically in the order of up to 5 cm, such as 2, 3, or 4 cm.

The lignocellulosic material may preferably be contacted with the CotA enzyme after washing and or steaming. This makes the material more accessible for the enzyme and increases the moisture content of the material. Hence, the invention relates to a method as described above, wherein the wood has a moisture content of at least 20% and is preheated to a temperature below 100 degrees Celsius before treating the wood with CotA laccase.

Without wanting to be bound by theory, it is reasoned herein that this washing and steaming step increases the performance of the enzyme resulting in a saving on energy in the entire process. This is indicated by the arrows 1, 2 and 3 in FIG. 7.

In certain processes, the temperature of the biomass or lignocellulosic material to be treated may be in excess of the enzyme inactivation temperature. Since a high temperature may inactivate enzymes by denaturing its amino acid chain, the enzyme may advantageously be added to the biomass at a point below the enzyme inactivation temperature. The enzymes may be added within the functional temperature range(s) or at the optimal temperature(s) of the enzyme. In case of biomass with a high temperature, the enzymes may be added after the biomass has cooled below the inactivation temperature and that the enzymatic process is completed sufficiently before the temperature has dropped below the optimal functional temperature of the enzyme. Naturally, it is also an option to maintain a desired temperature by cooling or heating the biomass or lignocellulosic material. Adding a dilution liquid, such as water at a certain temperature, may be used to cool the biomass.

In one embodiment, the enzyme pretreatment process may be performed at a specific temperature such as, for example at from 30 degrees C. to 80 degrees Celsius; 40 degrees C. to 70 degrees C.; or 45 degrees C. to 60 degrees C., such as 50 degrees C. or at room temperature or lower.

The contacting of the biomass with an enzyme can be performed for a period of time up to one day. While longer enzymatic digestions are possible, a shorter period of time such as 15 min 60 minutes, 1 hour, 2 hours, 3 hours or any time less than these values or any time between any of two of these values may be used for practical or economic reasons. In another preferred embodiment, the enzymatic digestions can take 50, 100, 150 or 200 hours or any time less than these values or any time between any of two of these values. See, e.g., the examples section. In one embodiment, a preferred period of enzyme contact is about 3 days or less.

CotA pretreatment may also advantageously be employed before or after an additional step of mechanical treatment usually referred to as low energy mechanical treatment (arrow 2). Therefore, in a particularly preferred embodiment, the invention relates to a method as described above wherein the treatment with CotA laccase is performed after washing and steaming of the biomass comprising lignocellulosic material and before or after a low energy mechanical treatment step but before the refining step.

In a CTMP processes, the CotA enzyme is preferably added during or after the chemical impregnation step to act together with other chemicals or enzymes, provided those chemicals and or enzymes do not interfere with laccase activity. In this case, the invention relates to a method as described above wherein the treatment with CotA laccase is performed during or after the chemical impregnation step and preferably continued after the impregnation step.

In another embodiment, in a CTMP processes, the CotA treatment is performed before the lignocellulosic material is treated with chemicals that dissolve the lignin. In this case, the invention relates to a method as described above wherein the treatment with CotA laccase is performed after washing and steaming of the biomass comprising lignocellulosic material but before the treatment with the chemicals.

In yet another embodiment, the lignocellulosic reject material is treated after the refining step. The residual lignocellulosic material, which was not sufficiently refined (reject), is usually fed into reject handling circuit for another refining operation (arrow 4 in FIG. 7). According to the present invention, this so-called reject material may advantageously be treated with CotA before being fed into the reject refining stage (FIG. 7). Hence, the invention relates to a method as described above, wherein the biomass comprising a lignocellulosic material is reject pulp.

The invention also provides new and improved enzymes and methods for its use. Hence, the invention also relates to a method as described above wherein the CotA laccase has a primary amino acid structure that is at least 60% identical to the sequence of COT1 (SEQ ID NO:1) or COT2 (SEQ ID NO:2). In a further improvement of the invention, the CotA laccase is COT1 (SEQ ID NO:1) or COT2 (SEQ ID NO:2).

The invention also relates to an isolated nucleic acid encoding a protein having laccase activity and a primary amino acid sequence that is at least 93% identical with the sequence of COT1 (SEQ ID NO:1) or COT2 (SEQ ID NO:2).

The invention also relates to an isolated polypeptide having laccase activity encoded by an isolated DNA sequence as described above. In a particularly preferred embodiment, the invention relates to an isolated polypeptide having laccase activity with a primary amino acid sequence that is at least 60% identical with the sequence of COT1 (SEQ ID NO:1) or COT2 (SEQ ID NO:2).

The invention also relates to lignocellulosic material, in particular wood chips comprising an isolated polypeptide or an isolated nucleic acid as described herein.

The skilled person will know how to obtain CotA laccases for use in the present invention. Laccases have been abundantly described and their primary amino acid structure is publicly available. They may be isolated from natural sources or be prepared by conventional recombinant DNA techniques. Dosage may easily be determined by trial and error methods for a given setting in a traditional pulp mill operation.

LEGEND TO THE FIGURES

Figure 1:
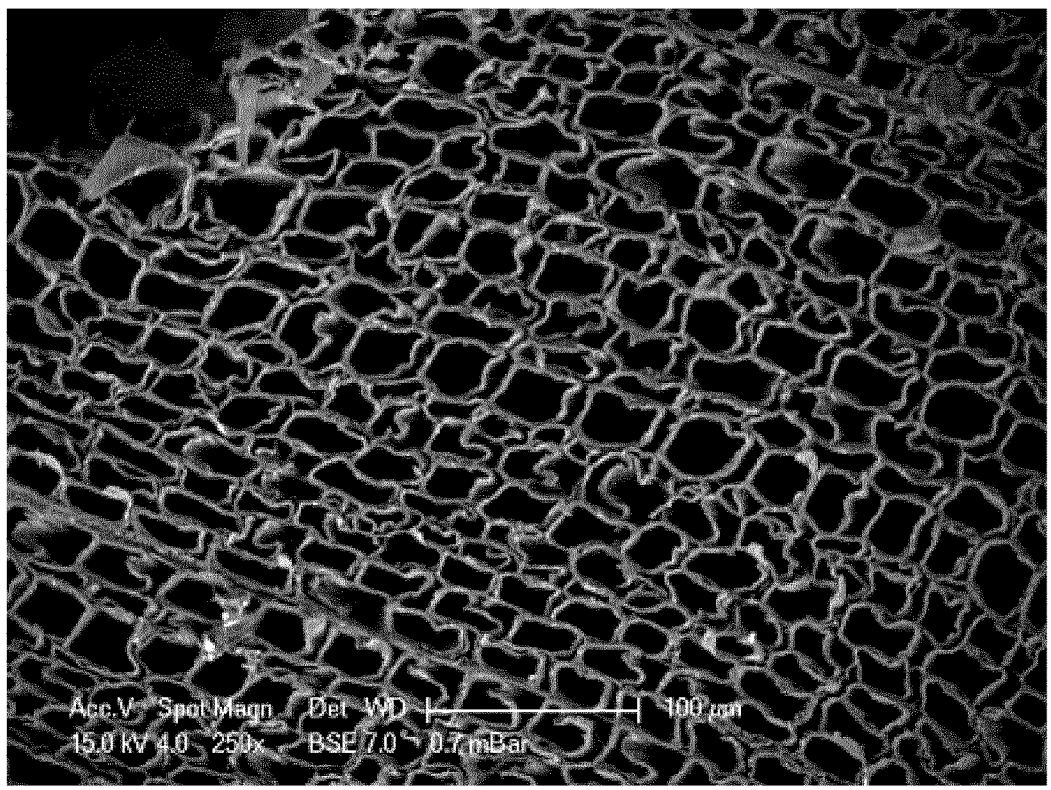
FIG. 1 shows an ESEM microscopy image of a section at the edge of a wood chip treated with CotA laccase.
Figure 1:
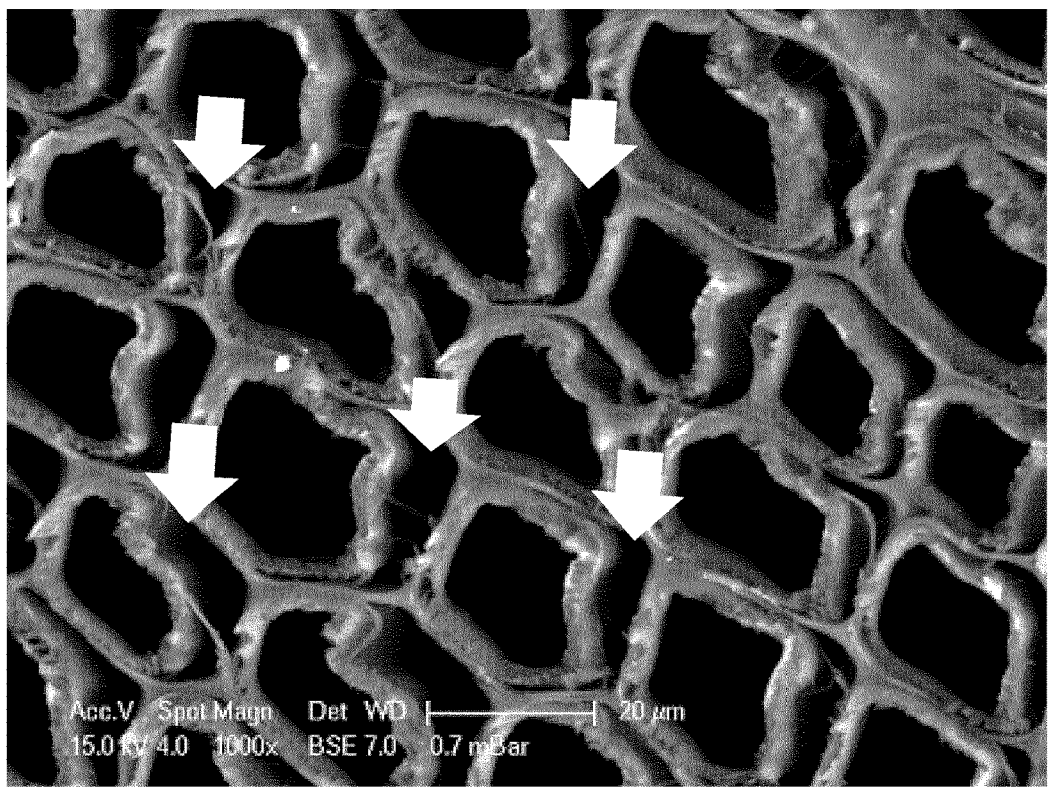
Figure 2:
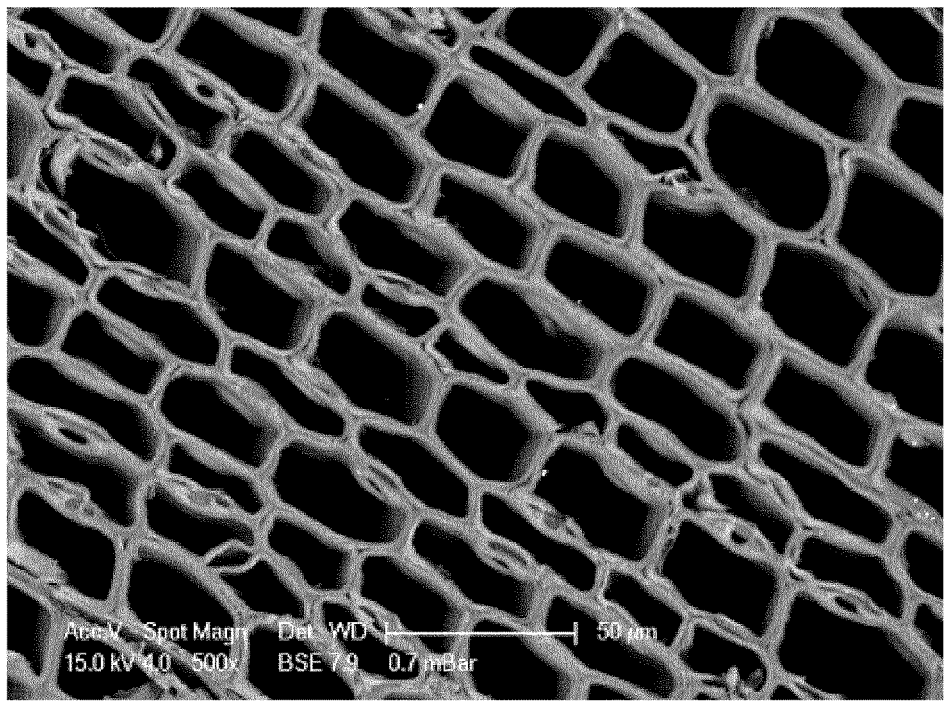
FIG. 2 shows an ESEM microscopy image of a section at the center of a wood chip treated with CotA laccase.
Figure 2:
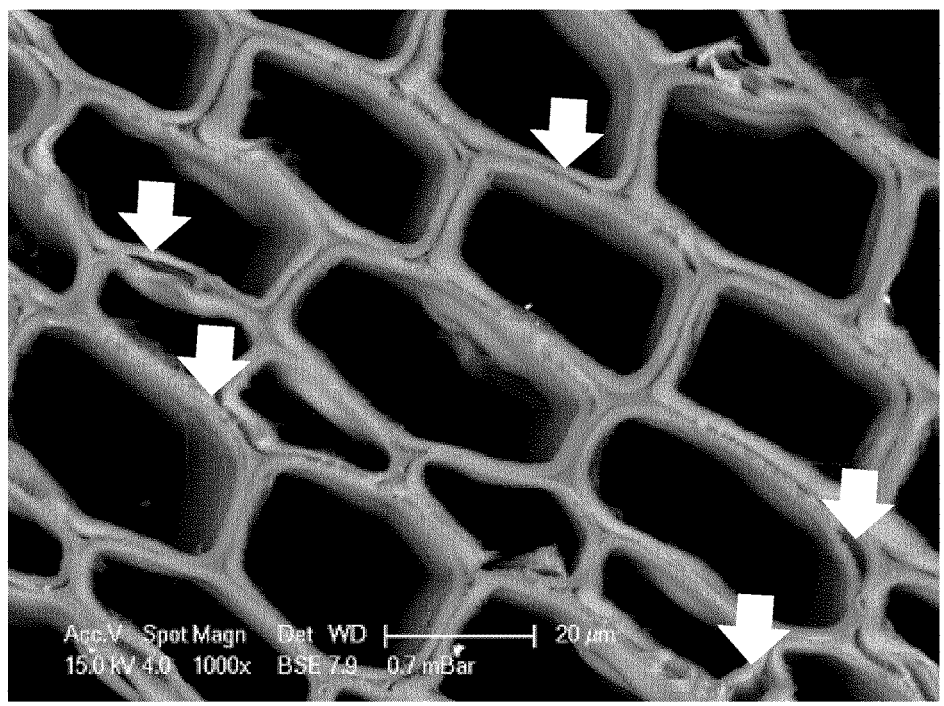
Figure 3:
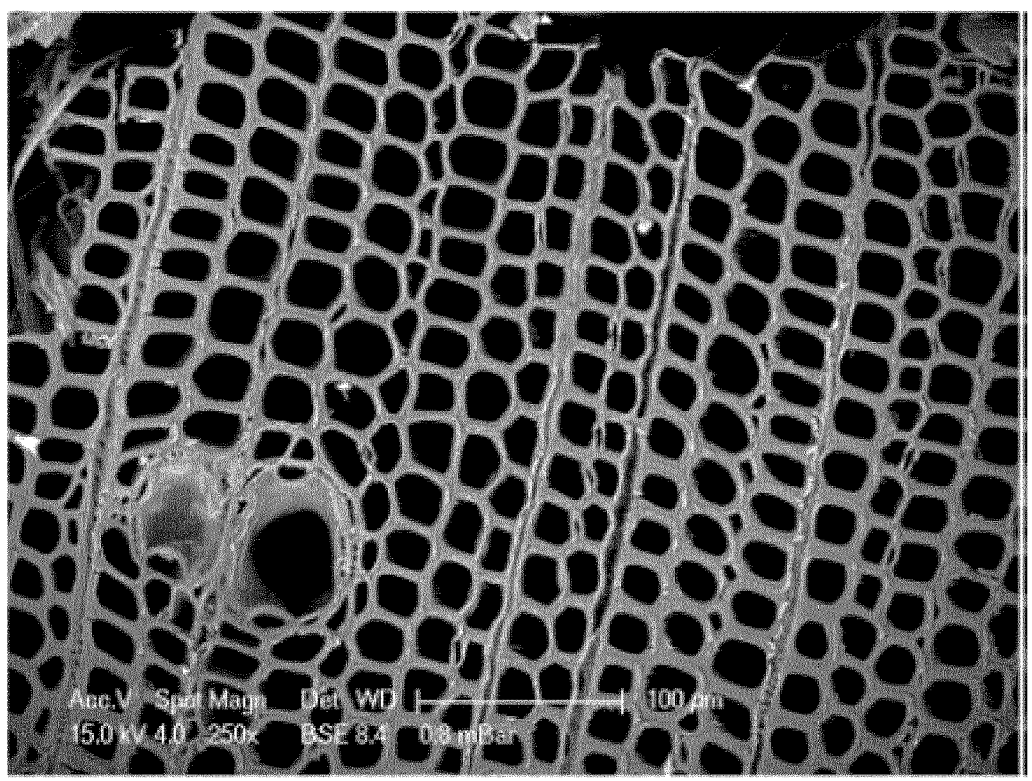
FIG. 3 shows an ESEM microscopy image of a section at the edge of a wood chip treated with a fungal laccase from *Trametes versicolor*.
Figure 3:
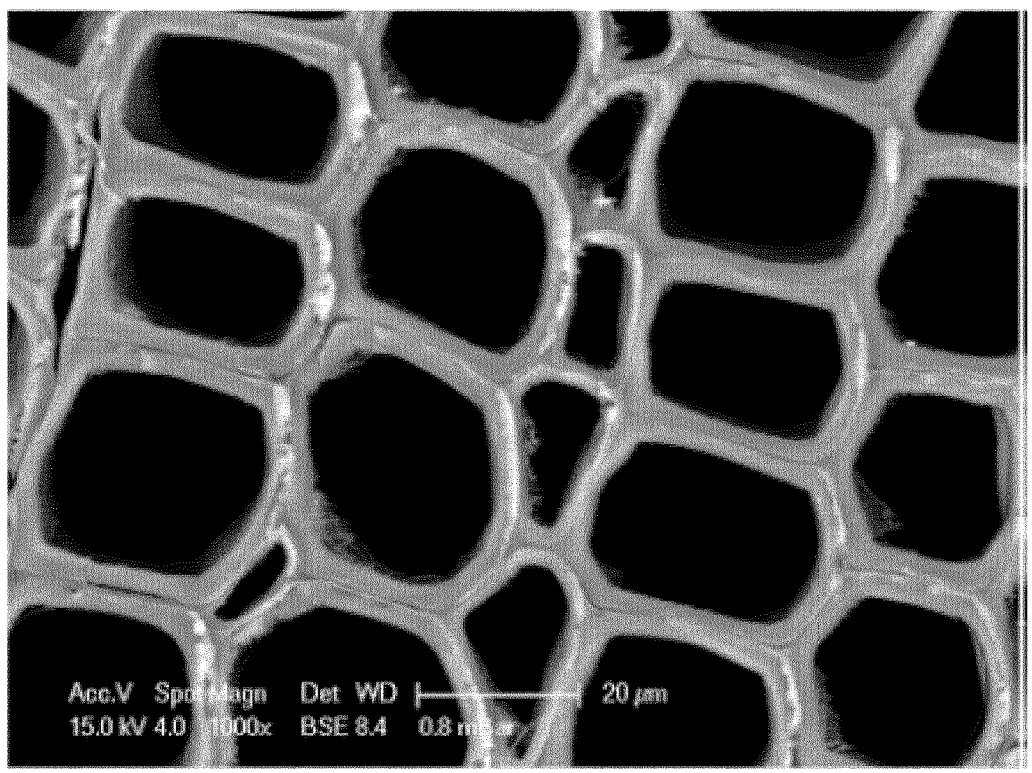
Figure 4:
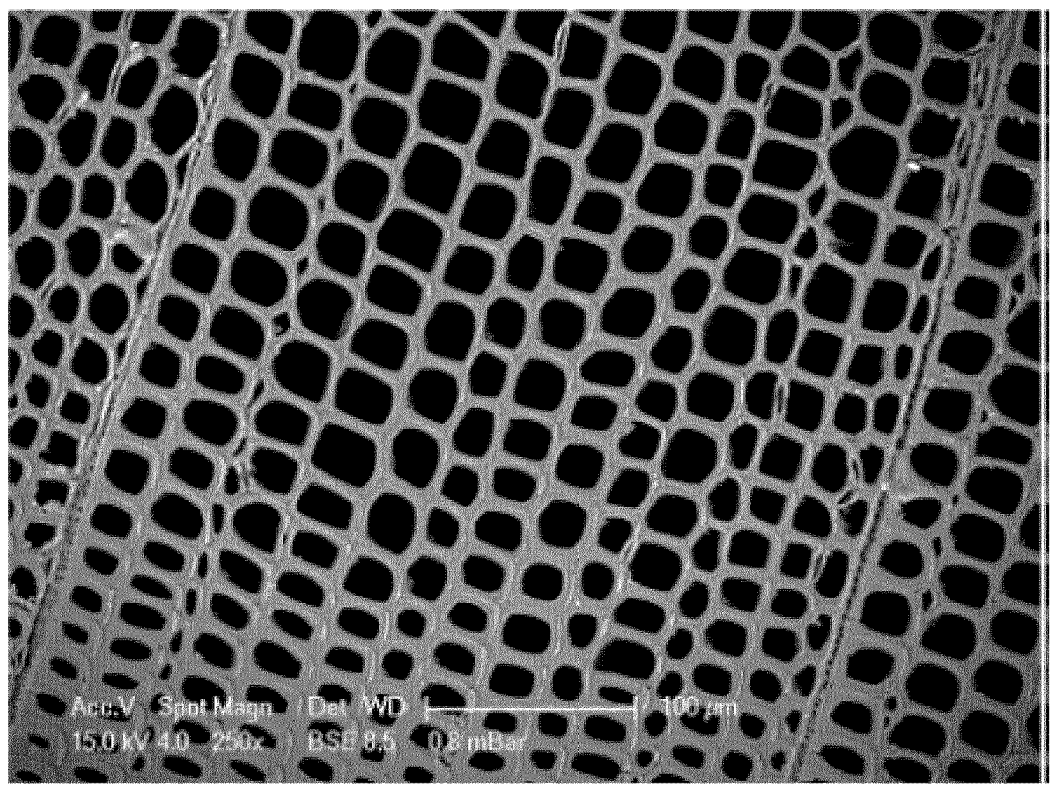
FIG. 4 shows an ESEM microscopy image of a section at the center of a wood chip treated with a fungal laccase from *Trametes versicolor*.
Figure 4:
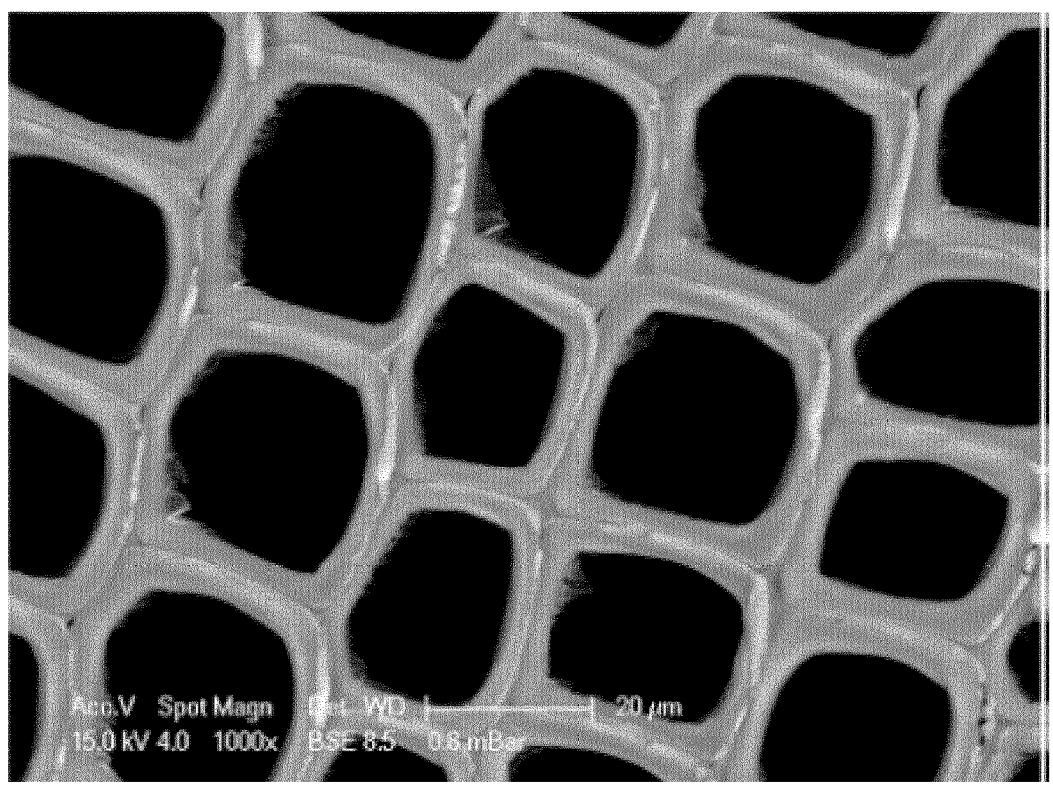
Figure 5:
FIG. 5 shows an ESEM microscopy image of a section at the edge of a wood chip treated with an *Escherichia coli* laccase CuEO.
Figure 5:
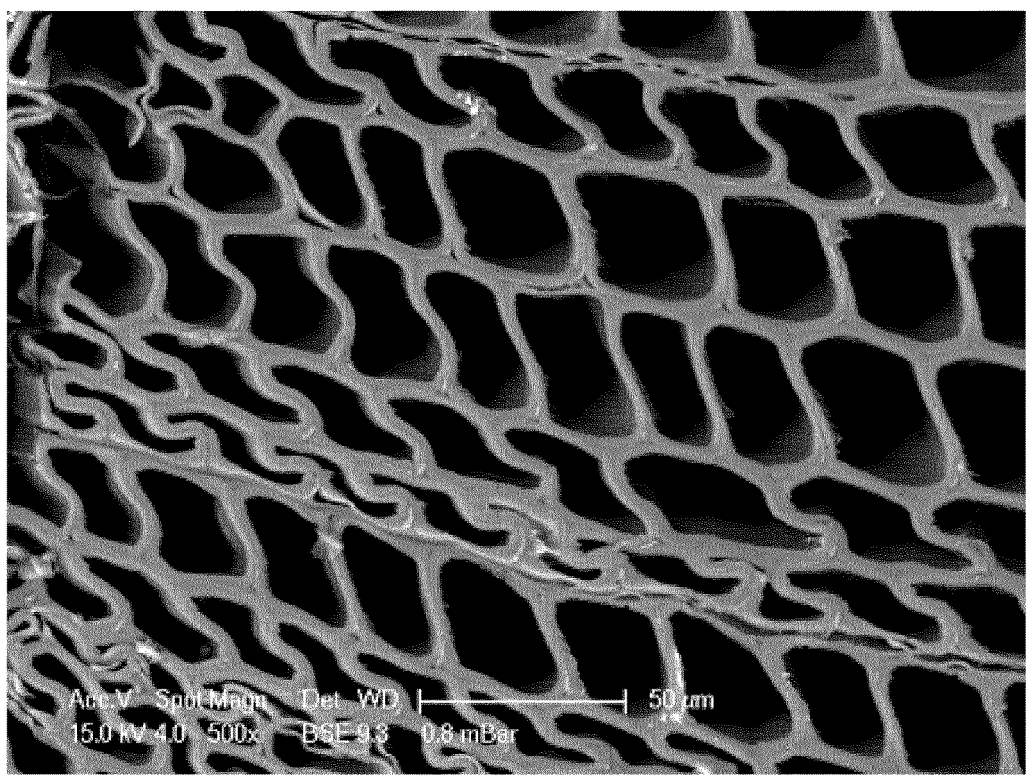
Figure 6:
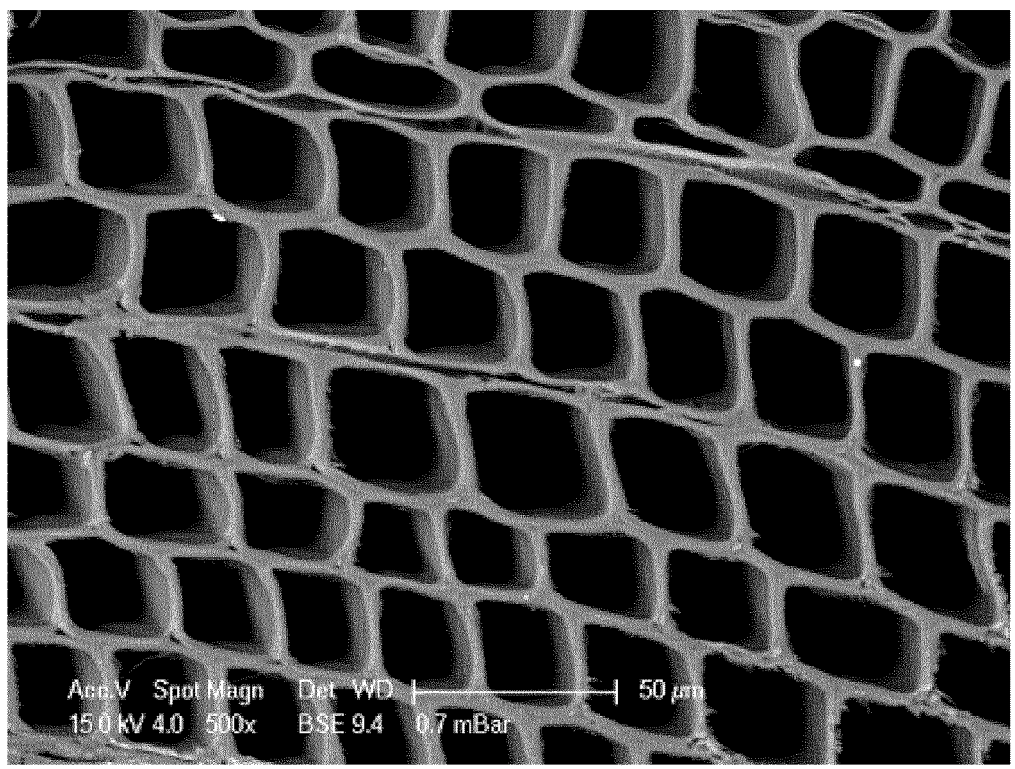
FIG. 6 shows an ESEM microscopy image of a section at the center of a wood chip treated with an *Escherichia coli* laccase CuEO.
Figure 6:
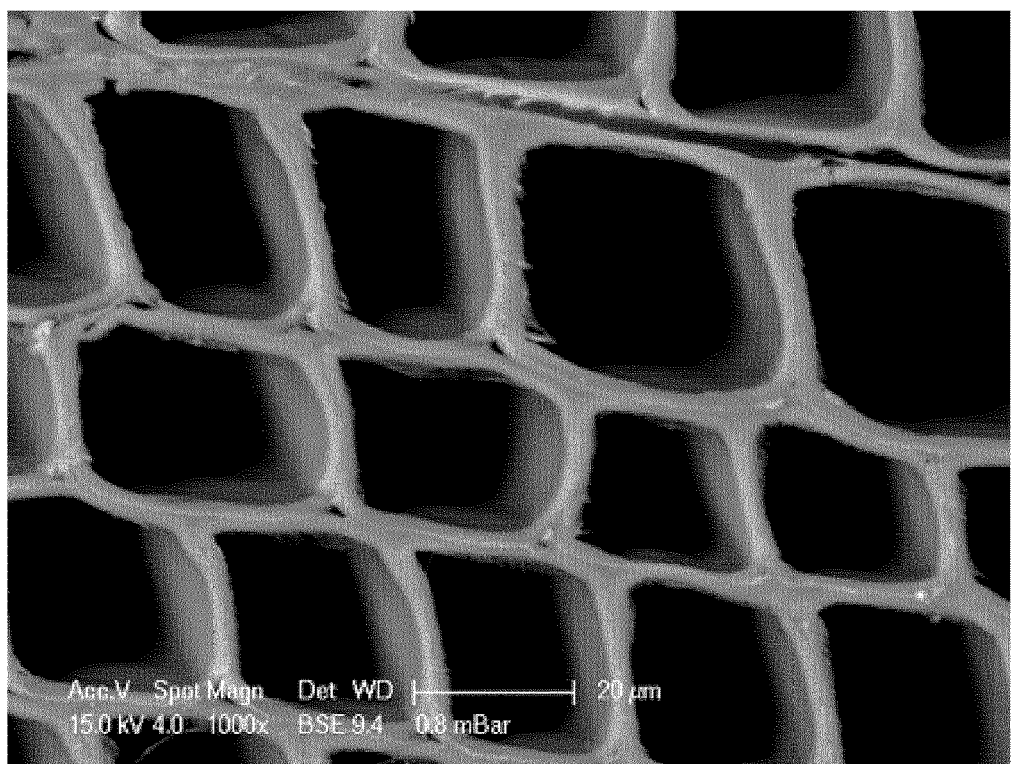
Figure 7:
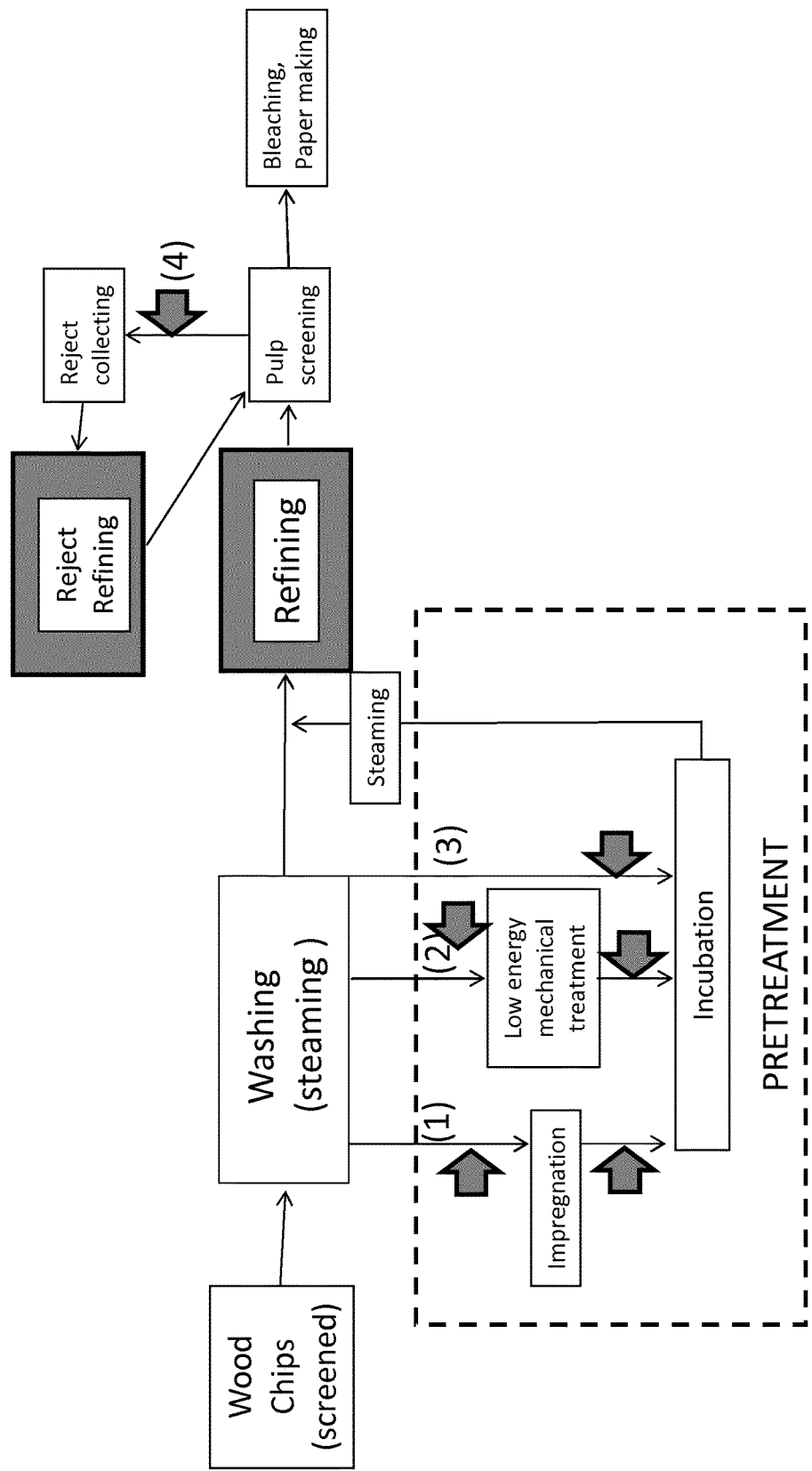

FIG. 7 Diagram of pulp manufacturing. Solid arrows indicate the positions in the process where CotA laccase treatment is beneficial for energy saving. The term screened chips means that the chips are selected for the appropriate and desired size. Washing means that they are cleaned with water to remove unwanted dust and dirt. Steaming means that the chips are subjected to steam. The figure shows three different pretreatment steps. First (position marked with (3)) the pretreatment consists of contacting the biomass containing lignocellulose with a CotA laccase (grey solid arrow). Second, the pretreatment may consist of contacting the biomass containing lignocellulose with a CotA laccase before or after low energy mechanical treatment (position marked with (2)). Thirdly, the pretreatment may consist of contacting the biomass containing lignocellulose with a CotA laccase before or after impregnation, for instance with a chemical reagent or a biological reagent such as an enzyme. Via an optional steaming step, the biomass containing the lignocellulose is then fed into the refining stage where the biomass is then heated to a temperature above 100 degrees Celsius and refined, i.e. subjected to mechanical defibration. After the refining step the resulting pulp is screened for residual lignocellulosic material where wood fibers were not sufficiently separated. That material (reject) is then fed into the reject refining process. CotA may advantageously be applied to the reject pulp in order to save energy in the reject refining process.

Figure 8:
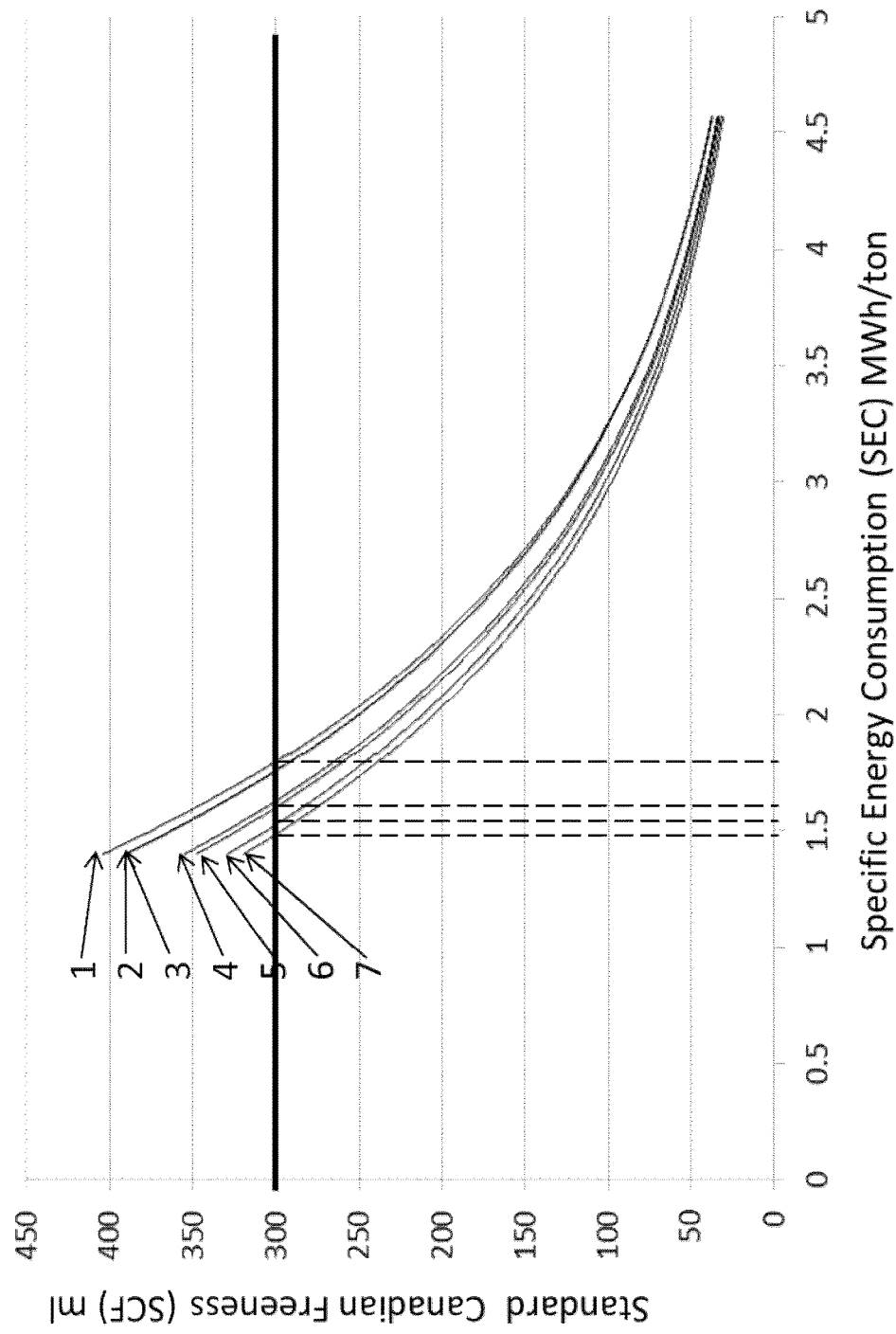

FIG. 8: Energy curves (Pulp freeness plotted against specific energy consumption) from refining experiment (example 2).

The graph shows a shift of the energy line to the left (or down) in the samples treated with COTA laccase, meaning that energy saving is achieved. In other words, the same freeness (as for example taken here at 300 ml, indicated in the figure by a horizontal line) can be obtained with less energy. Curves correspond to the following samples 1-*Trametes versicolor* (0.05 u/ml), 2—Reference, 3—*Trametes versicolor* (0.1 u/ml), 4—COT1 (0.05 u/ml), 5—COT2 (0.05 u/ml), 6—COT2 (0.1 u/ml), 7—COT1 (0.1 u/ml)

EXAMPLES

Example 1: Microscopy

Wood chips of 50 g dry matter content (DMC) with a largest size between 35 mm and 40 mm mm were washed to remove residual dirt. and thereafter treated with steam for 10 minutes. Chips were than equilibrated to 50 degrees C., placed in a cylindrical device with a press. Mechanical pressure was applied from the top 63.5 kPa/cm$^2$, until the layer of chips was half of the original height. Any liquid coming out of the chips was drained though small holes at the bottom of the cylinder. After that, the pressure was slowly released and the enzyme solution fed from the bottom of the cylinder. The enzyme solution contained 1 unit/ml of one of the laccase enzymes (as indicated) in 20 mM Succinic acid pH 5.0. A catalytic unit is defined as the amount of enzyme needed to convert 1 micromole of substrate (ABTS) in 1 min.

The following laccases were used herein: (1) Spore coat protein from *Bacillus subtilis* CotA (COT2 (SEQ ID NO:2, recombinantly expressed in *E. coli*), (2) commercially available fungal laccase from from white-rot-fungi *Trametes versicolor* (available from Sigma-Aldrich), and (3) laccase from *E. coli* termed CUEO, recombinantly expressed in *E. coli*.

Approximately 30 ml of this solution was absorbed by the chips. Any residual solution was drained. These chips were then placed in a sealed container to prevent evaporation and incubated for 2 hours. Samples with COT2 and CUEO laccases were incubated at their optimal temperature, i.e. 70 degrees Celsius, sample with *Trametes versicolor* laccase was incubated at 50 degrees Celsius since *Trametes versicolor* laccase would be quickly inactivated at 70 degrees Celsius.

From each sample, four chips were taken out and cut approximately in the middle. The cut surface was then sectioned manually by a razor blade and left to dry at room temperature.

The chip cross-sections were imaged using a Philips XL30 ESEM-FEG (Environmental Scanning Electron Microscope-Field Emission Gun). Working conditions were as follows: low vacuum mode, 0.7 mbar pressure in the sample chamber, BSE detector (backscattered electrons) and 15 kV acceleration voltage. The magnifications used were 200×, 250×, 500× and 1000×.

Example 2: Energy Saving in TMP

A series of laboratory scale refining experiments was performed in order to evaluate the effect of laccase pretreatment on refining energy.

Screened wood chips with an average maximum size of approximately 40 mm were impregnated with a solution containing either one of two CotA laccases (COTA laccases (COT1 and COT2, SEQ ID NO: 1 and SEQ ID NO: 2 resp.) or a commercially obtained fungal laccase from from white-rot-fungi *Trametes versicolor* (available from Sigma-Aldrich).

The impregnation of wood chips was done in portions of 50 g DMC as described in example 1, with the exception that two concentrations of impregnation solution were used; 0.1 u/ml or 0.5 u/ml of laccase in 20 mM Succinic acid pH 5. Reference sample was impregnated with the same solution without laccase.

Three portions of 50 gram (DMC) of impregnated chips were produced with each dosage of each laccase. After impregnation, the portions treated with the same enzyme were combined to a single sample of 150 gram DMC.

Impregnated chips were then placed in a sealed container to prevent evaporation and incubated for 1 hour. Samples with COTA laccases were incubated at their optimal temperature, i.e. 70 degrees Celsius, sample with *Trametes versicolor* laccase was incubated at 50 degrees Celsius since *Trametes versicolor* laccase would be quickly inactivated at 70 degrees Celsius.

The treated wood chips described above were portioned into 125 g DMC batches and refined in a low-intensity wing refiner comprising a wing defibrator chamber. The wing defibrator chamber consisted of two rotating blades which rotate in opposite axial directions. A 20 blade cylindrical structure rotated within a distance of 1 mm from 4 wing-like rotating blades.

The refiner was heated and three empty runs were used as blank. The steaming temperature was 124° C.±0.6° C. The wood chips were steamed for 5 minutes, during which the 4 wing-like blades were rotated 90° every 1.25 minutes to heat the chips evenly. After 2 minutes of steaming the condensate was let out during 10 seconds. After 4 minutes and 50 seconds of steaming the valve was closed, puls-meter zeroed and the run started after 5 minutes of steaming. The experiments were done for 2, 4, 6, and 8 minutes of refining. When the time had passed, the experiment was stopped directly when the puls-meter changed value. The pressure in the chamber was 1.9-2.6 bars and the temperature rising from about 124° C. to 136° C., depending on how long the experiment was continued. All enzymatic trials were run in singles, as well as 2, 6, and 8 minutes for the reference. 4 minutes of refining for the reference was run 4 times.

After refining, the pulps were centrifuged and measured for dry matter content DMC (according to SCAN-C 3:78) and freeness was determined with a Canadian Standard Freeness tester. The results are shown in table 1. The total amount of consumed energy was plotted against freeness (FIG. 8) and trend lines were calculated for the reference, COT1, COT2 and *Trametes versicolor* (R=0.99; 0.97; 0.99; and 0.99 respectively). The energy consumption was compared at constant levels of freeness (300 ml).

Fungal laccase had no significant effect of energy consumption in this refining experiment. In contrast, COT1 and COT2 samples showed very similar significant reduction in energy consumption about 7-8% for 0.05 u/ml dosage and 13-15% for 0.1 u/ml dosage. This energy saving values are highly industrially relevant and considering the low dosing of enzyme, this may be considered of high commercial importance.

TABLE 1 refining energy at 300 ml freeness from reference and laccase treated samples.

| Curve No | Sample | SEC at 300 ml freeness | Energy saving (%) |
| --- | --- | --- | --- |
| 2 | Reference | 1.73 | 0 |
| 1 | Tv* (0.05 u/ml) | 1.75 | −0.61 |
| 3 | Tv (0.1 u/ml) | 1.74 | 0.10 |
| 4 | COT1 (0.05 u/ml) | 1.62 | 6.8 |
| 7 | COT1 (0.1 u/ml) | 1.47 | 14.9 |
| 5 | COT2 (0.05 u/ml) | 1.59 | 8.3 |
| 6 | COT2 (0.1 u/ml) | 1.50 | 13.2 |

*Tv = *Trametes versicolor* laccase.

The invention claimed is:

1. A method for recovering cellulose from a biomass comprising lignocellulosic material, the method comprising:
    contacting the biomass with a CotA laccase prior to heating the biomass to a temperature above 100 degrees Celsius;
    heating the biomass to a temperature above 100 degrees Celsius;
    subjecting the heated biomass to mechanical defibration; and
    wherein the CotA laccase has a primary amino acid structure having at least 99% sequence identity to the sequence of COT1 (SEQ ID NO:1).

2. The method according to claim 1, wherein the lignocellulosic material comprises wood.

3. The method according to claim 2, wherein the wood is a wood chip.

4. The method according to claim 2, wherein the wood is a destructured wood chip.

5. The method according to claim 1, further comprising treating the biomass comprising the lignocellulosic materials with a chemical composition before the biomass is defibrated.

6. The method according to claim 5, wherein the chemical is able to degrade lignin.

7. The method according to claim 2, wherein the wood has a moisture content of at least 20% and is preheated to a temperature below 100 degrees Celsius before treating the wood with CotA laccase.

8. The method according to claim 7, wherein the wood is preheated to a temperature below the inactivation temperature of the CotA laccase.

9. The method according to claim 7, wherein the treatment with CotA laccase is performed after a low energy mechanical treatment step.

10. The method according to claim 7, further comprising an impregnation step wherein the biomass comprising lignocellulosic material is contacted with a chemical composition or an enzyme before or after the biomass is contacted with the CotA laccase.

11. The method according to claim 1, wherein the biomass comprising a lignocellulosic material is reject pulp.

12. A method for recovering cellulose from a biomass comprising lignocellulosic material, the method comprising:
    contacting the biomass with a CotA laccase prior to heating the biomass to a temperature above 100 degrees Celsius;
    heating the biomass to a temperature above 100 degrees Celsius; and
    subjecting the heated biomass to mechanical defibration;
    wherein the CotA laccase has a primary amino acid structure having at least 98% sequence identity to the sequence of COT1 (SEQ ID NO: 1).

13. A method for recovering cellulose from a biomass comprising lignocellulosic material, the method comprising:
    contacting the biomass with a CotA laccase prior to heating the biomass to a temperature above 100 degrees Celsius;
    heating the biomass to a temperature above 100 degrees Celsius; and
    subjecting the heated biomass to mechanical defibration;
    wherein CotA is COT1 (SEQ ID NO:1) or COT2 (SEQ ID NO:2).

14. A method for recovering cellulose from a biomass comprising lignocellulosic material, the method comprising:
    contacting the biomass with a CotA laccase prior to heating the biomass to a temperature above 100 degrees Celsius;
    heating the biomass to a temperature above 100 degrees Celsius; and
    subjecting the heated biomass to mechanical defibration;
    wherein the CotA laccase has a primary amino acid structure having at least 99% sequence identity to the sequence of COT2 (SEQ ID NO:2).

* * * * *